US009956398B2

(12) United States Patent
Callegari et al.

(10) Patent No.: US 9,956,398 B2
(45) Date of Patent: May 1, 2018

(54) IMPLANTABLE LEAD INCLUDING A CUFF FOR NERVE STIMULATION

(71) Applicant: SORIN CRM SAS, Clamart (FR)

(72) Inventors: Vincent Callegari, Corbais (BE); Hervé Mével, Chastre (BE); Stéphane Béfahy, Brussels (BE)

(73) Assignee: Sorin CRM SAS, Clamart (FR)

( * ) Notice: Subject to any disclaimer, the term of this patent is extended or adjusted under 35 U.S.C. 154(b) by 369 days.

(21) Appl. No.: 14/747,975

(22) Filed: Jun. 23, 2015

(65) Prior Publication Data
US 2015/0374975 A1    Dec. 31, 2015

(30) Foreign Application Priority Data

Jun. 25, 2014  (FR) ...................................... 14 55895

(51) Int. Cl.
*A61N 1/05* (2006.01)

(52) U.S. Cl.
CPC .............. *A61N 1/0556* (2013.01); *A61N 1/05* (2013.01); *A61N 1/0551* (2013.01); *A61N 1/057* (2013.01)

(58) Field of Classification Search
CPC ...... A61N 1/0556; A61N 1/0551; A61N 1/05; A61N 1/057
USPC .................................................. 607/118, 152
See application file for complete search history.

(56) References Cited

U.S. PATENT DOCUMENTS

| 4,602,624 A * | 7/1986 | Naples ................. A61N 1/0556 607/118 |
| 2009/0210042 A1 | 8/2009 | Kowalczewski |
| 2010/0036451 A1 * | 2/2010 | Hoffer ................. A61N 1/0558 607/42 |

FOREIGN PATENT DOCUMENTS

| DE | 1020070 36 862 | 2/2009 | |
| DE | 102007036862 A1 * | 2/2009 | ........... A61N 1/0556 |
| EP | 0 865 800 | 9/1998 | |

OTHER PUBLICATIONS

Preliminary Search Report for French Patent Application No. 1455895, dated Dec. 19, 2014, 1 page.

* cited by examiner

*Primary Examiner* — Michael Carey
(74) *Attorney, Agent, or Firm* — Foley & Lardner LLP

(57) ABSTRACT

A cuff for use in nerve stimulation includes a sheet of elastomer having at least one electrode and being pre-stressed so as to allow its spiral self-winding to form a cuff around the nerve. The sheet is delimited by a first width defining an outer edge of the cuff after winding, a second width defining an opposite inner edge, a first length and a second opposite length. The first width is at both ends connected to the two lengths by a respective bevel edge forming an oblique angle relative to the direction of greatest dimension of the sheet.

18 Claims, 2 Drawing Sheets

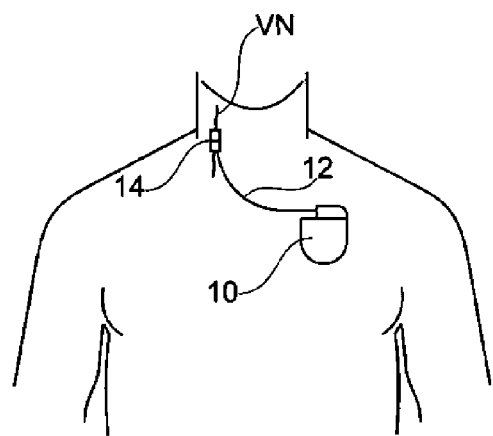
Fig. 1
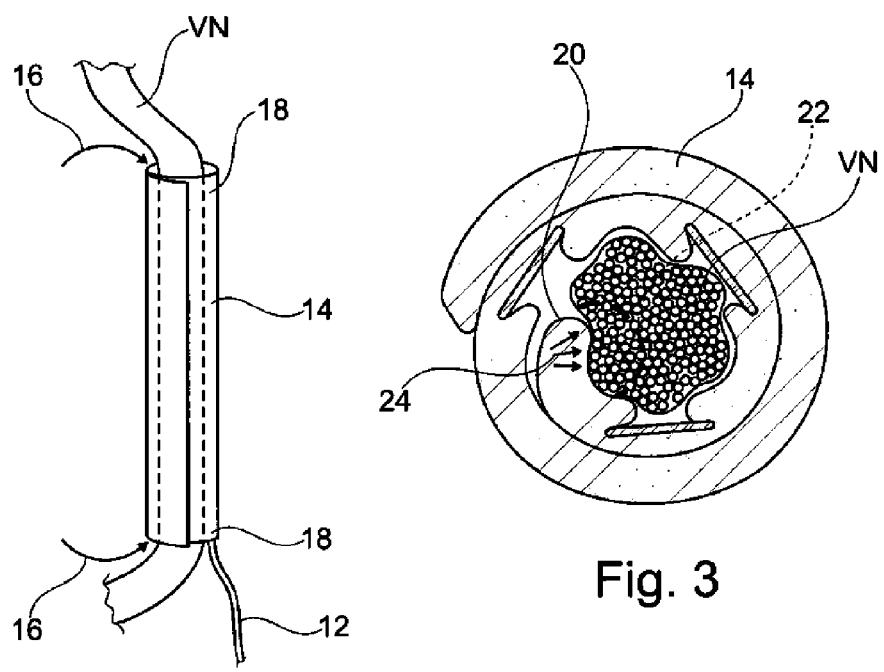
Fig. 2
Fig. 3

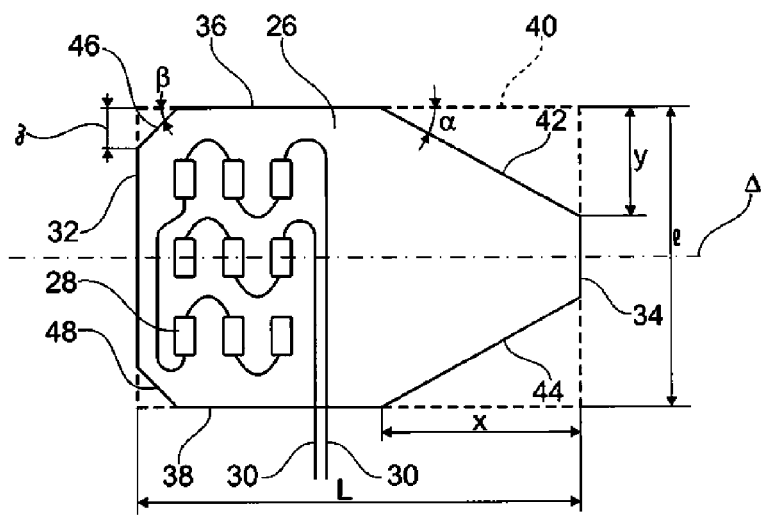
Fig. 4
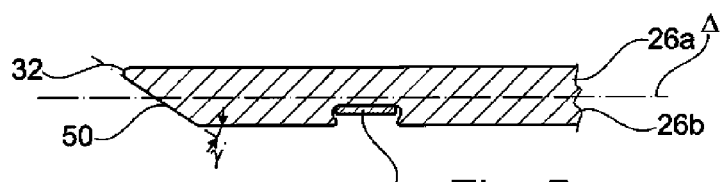
Fig. 5
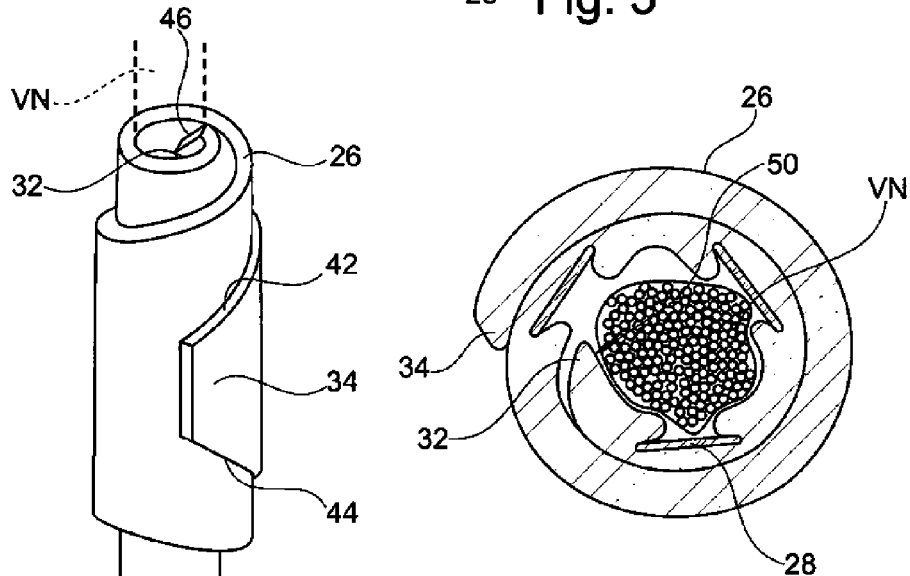
Fig. 6
Fig. 7

IMPLANTABLE LEAD INCLUDING A CUFF FOR NERVE STIMULATION

CROSS-REFERENCE TO RELATED PATENT APPLICATIONS

This application claims the benefit of and priority to French Patent Application No. 1455895, filed Jun. 25, 2014, which is hereby incorporated by reference herein in its entirety.

BACKGROUND

The invention relates to "active implantable medical devices" as defined by Directive 90/385/EEC of 20 Jun. 1990 of the Council of the European Communities, specifically implants for stimulation of an elongated cylindrical organ and/or the collection of electrical potentials on such an organ. The invention relates more particularly to the stimulation of nerves, especially the vagus nerve stimulation, in the case of VNS (Vagus Nerve Stimulation) therapy. However, this application is in no way limiting, the invention being possibly used for stimulation/detection of any other organ, or for other purposes such as local delivery of an active agent, etc. to this organ, when the target organ has an elongated cylindrical shape.

The nervous system stimulation therapy is recognized in respect of many disorders such as epilepsy, pain, heart failure, sleep apnea, obesity, etc. The devices used for this purpose include a lead provided with an electrode implanted on the vagus nerve and a generator delivering electrical pulses to this electrode.

VNS therapy typically involves the generation of repetitive pulse bursts, synchronized or not on heart rate depending on the condition to be addressed, these pulses being superimposed on the signals naturally conveyed by the nervous system, and possibly organized in a closed loop. The vagus nerve stimulation may act in efference, directly into an organ, or in afference, to the brain to affect the central nervous system. The waveform of VNS pulses is intended to be interpreted by the central nervous system as a solicitation to produce the expected effects, by prompting the central nervous system to attempt to compensate in opposition to the generated signals.

The invention more particularly relates to a device implanted at the electrode/nerve interface, thereby maintaining the electrode in contact with the nerve or adjacent thereof. Given the approximately cylindrical elongated configuration of a peripheral nerve such as the vagus nerve, the most commonly used device is in the form of a tubular cuff wrapped around the nerve. The cuff is generally made of an elastomer such as silicone, because of the excellent biocompatibility of this material, and it carries on its inner face, applied against the nerve, the stimulation (and/or detection) electrodes.

Such a cuff is, for example, disclosed in U.S. Pat. No. 4,602,624. The cuff described in this document is made from two elastomeric sheets laminated together, one of which being stretched in advance in a preferred pre-stress direction. The resulting composite cuff is then cut to give a rectangular part which, due to the pre-stressing of the one of the sheets, will naturally tend, in the free state, to be wound in a spiral on itself around an axis perpendicular to the biasing direction (a "spiral" being a plane curve being wound regularly around a point from which it deviates more and more).

Compared to a rigid cuff, the cuff described herein has the advantage of simplicity of implementation. The surgeon has just to place it, pass it under the nerve then release it so that it comes from itself to be wrapped around the nerve. Moreover, the cuff is self-adaptive. Indeed, immediately after implantation a normal inflammatory process produces a temporary swelling of the nerve, which then disappears. If one chooses a flexible spiral cuff with an inside diameter slightly smaller than the diameter of the nerve rest, the cuff—with electrodes—always remain closely pressed against the nerve even if the diameter of the latter varies, and without risk of excessive compression that may irreversibly deteriorate nervous tissue.

This device is nevertheless not devoid of drawbacks. A first drawback is present at the time of implantation. To implant the cuff after reaching the target nerve, the surgeon pulls the nerve out of the incision that he created, to slide the unrolled cuff at the selected location. During this maneuver, the tension on the nerve can lead locally to the ends of the sleeve, to relatively high stresses on nerve tissue that can damage them. Another possible cause of the nerve damage is the duration of the procedure, which may expose the nerve to air for too long. It is therefore necessary that the cuff implantation procedure is very short, limiting as much as possible the manipulation of the nerve. Also during implantation, the corners of cuff tend to wind on themselves and impede implantation, which complicates the task of the surgeon.

A second drawback, which appears after implantation, is due to the fact that the innermost edge of the cuff, that is to say, the rolled edge around the nerve bears against the latter and exerts along the contact line pressure which tends to force or even distort the nerve. The risk also exists that during implantation the surgeon allowed the outer edge of the cuff to roll in the opposite direction, which then forms a second turn in the opposite direction to the first. The radius of curvature is no longer the one that was expected, with consequently potential complications.

Finally, a third drawback is linked to the manufacturing process. As mentioned above, the cuff is made by laminating together two elastomeric sheets, with a directional pre-stress applied to one of them. These sheets being very thin (their typical thickness is about 100 µm), problems of homogeneity of the material and of thickness tolerance can appear in the extent of the surface of a same sheet as well as between two sheets, limiting the reproducibility of the production process of the cuffs. It is certainly possible to overcome this disadvantage by using large sheets, but with a negative impact on the industrial process. It is also possible to use thicker sheets, more easily controllable during the process, but with an increased damage risk of the nerve due to less flexibility and therefore the lesser ability of the cuff to conform to the morphology of the nerve in the implantation zone.

Another type of cuff is disclosed in DE 10 2007 036 862 A1, which discloses a strip-shaped elongate element of flexible material (silicone) carrying one or two electrodes formed in a central region. This strip is further provided on one side of the central region, of a hole or of a transverse slot, and the opposite side has a tapered shape which, after winding around the nerve, may be introduced into the slot so as to grip the cuff on the nerve, like a cable tie imprisoning an electrical wire harness.

Compared to the first type of cuff described above, this second type has multiple drawbacks:

It is not a "self-rolling" cuff, in that it is not sufficient to unwind and to release it for it comes by itself in position as a spiral around the nerve. It rather requires a manipulation of the surgeon to introduce the tapered end into the slot and secure the cuff around the nerve;

It leaves two long projections extending radially from the implantation site (the portion bearing the slot, and by the portion tapered after insertion into the slot);

The position of the electrodes in a central region of the ribbon complicates the accurate placement of these electrodes at the selected stimulation site;

It is not "self-adapting." The degree of tightening varies with the diameter of the nerve, which may change, for example under the effect of a temporary swelling reaction after implantation; and The degree of tightening the cuff on the nerve is totally operator-dependent since the tightening depends on the length of the protruding portion of the slot—hence a possible insufficient tightening (leading to incorrect application of electrodes against the nerve) or, conversely, excessive tightening (with the risk of irreversible damage to nerve tissue).

The need therefore exists for a self-rollable thin elastomeric cuff which can be produced by an effective industrial method, with a high degree of reproducibility, without the use of thick sheets that lead to products that are not fully satisfactory in terms of use.

SUMMARY

One object of the invention is to solve these problems by proposing a new spiral self-rollable cuff structure that (a) facilitates rapid implantation by the surgeon, without introducing excessive stresses on the nerve; (b) respects the anatomic integrity of the nerve after implantation, while continuing to ensure adequate positioning of the cuff to the chosen implantation site; and (c) can be produced by an optimized method from the standpoint of industrial constraints.

To this end, one embodiment of the invention provides an implantable lead comprising a self-rollable cuff, as described in particular by the U.S. Pat. No. 4,602,624 cited above, to be wound around an elongate cylindrical body such as a nerve, and including an elastically deformable material sheet having at least one detection/stimulation electrode on a first face of the sheet. The sheet is biased so as to allow a self-winding, from an initial position wherein the sheet is held under stress in the deployed state, to a final position wherein the sheet is loosely wound in spiral to form a cuff around the organ, with the first face carrying the electrodes facing inwards. The sheet is delimited by a first width defining an outer edge of the cuff after winding, an opposite second width defining an inner edge of the cuff after winding, a first length bringing together the first homologous ends of the first and of the second widths, and a second opposite length bringing together the second homologous ends of the first and second width.

In one embodiment of the invention, the first width is at its two ends connected to the two lengths by a respective bevel edge (that is to say an obliquely cut edge instead of being at right angles to shoot down this angle) forming an oblique angle relative to the direction of greatest dimension of the sheet.

According to various advantageous embodiments:

The bevel edge forms with respect to the direction of greatest dimension of the sheet an angle between 20 and 45°, and/or it extends over 15 to 60% of the extent of the sheet in its direction of its largest dimension and/or 20 to 50% of the extent of the sheet perpendicularly to its direction of largest dimension;

The second width is, at both ends, connected to the two lengths by another respective bevel edge forming an oblique angle relative to the direction of larger dimension of the sheet and/or forming with respect to the direction of largest dimension of the sheet an angle between 30 and 60°, and/or extending over 10 to 25% of the extent of the sheet perpendicularly to its direction of largest dimension;

The edge of the sheet in the region of the first width is a beveled edge in the direction of thickness, the bevel being oriented toward said first side facing inwardly; and The bevel forms with respect to the direction (Δ) of greatest dimension of the sheet an angle between 20 and 45°.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which:

FIG. 1 is an overview presentation of a VNS stimulation system, showing the generator and the vagus nerve, as well as the used lead.

FIG. 2 is a view of a cuff according to the prior art, wrapped around the vagus nerve during the implantation procedure.

FIG. 3 is an enlarged cross section of the assembly formed by the cuff of FIG. 2 wrapped around the vagus nerve, in particular showing the stresses that the sleeve can exert on the nerve.

FIG. 4 is a plan view of the cuff according to the invention, in the unrolled configuration as this cuff is during manufacturing.

FIG. 5 is a section in the thickness direction of the cuff of FIG. 4, in a partial view in the region of one of the edges, in particular showing the two-layered structure laminated together.

FIG. 6 is a perspective view of the cuff of FIG. 4 in its open configuration, wound on itself.

FIG. 7 is an enlarged cross-section, similar to FIG. 3, of the assembly formed by the cuff of the invention wrapped around the vagus nerve.

DETAILED DESCRIPTION

We will now describe an embodiment of the invention, as a lead for vagus nerve stimulation, this example being in no way limiting as was mentioned in the introduction. In FIG. 1 reference 10 denotes the housing of an implantable generator of VNS stimulation. The generated pacing pulses are delivered by a lead carrying at its distal portion a cuff 14 provided with electrodes applied against the vagus nerve VN to stimulate the latter by the pulse bursts produced by the generator 10.

FIG. 2 is a view of a cuff 14 according to the prior art, wrapped around the vagus nerve VN during the implantation procedure. To place the cuff shown in FIG. 2, the surgeon had to pull the vagus nerve VN out of the incision he had practiced, to be able to slide the unrolled cuff in the chosen location. After spiral self-winding, the cuff 14 is as shown in FIG. 2. In this particular configuration, the stresses are exerted by the cylindrical cuff in the region 16 due to the rigidity discontinuity between the part of the nerve enclosed inside the cuff 14, and the free portion beyond the cuff. This discontinuity between a part wherein the nerve is immobilized and that wherein it is free may locally create stresses at the transition point, stresses that could damage nerve tissue.

Another drawback, also specific to the cuffs of the prior art, is that if one considers the innermost end of the spirally wound cuff 20, this end being sandwiched by the remainder of the cuff, it has the effect of exercise stress on the VN nerve in the region 22 in the vicinity of the end (constraints schematized by arrows 24), which may have the effect of distorting the nerve, with potentially harmful effects. These various drawbacks, as well as those exposed in the introduction, can be solved by a cuff made according to the teachings of the invention, illustrated in FIGS. 5 to 7.

FIG. 4 is a plan view of a cuff 26 according to one embodiment of the invention, in an unrolled configuration as the cuff is during manufacturing. The cuff 26 is made from two elastomeric sheets 26a and 26b (FIG. 5) laminated together, for example of silicone, one of the sheets having been subjected beforehand to a stretching pre-stressing in the direction A, which in this example is the direction of greatest dimension of the sheet 26.

As explained in U.S. Pat. No. 4,602,624 cited above, this technique can make the spiral cuff self-rollable when the sheet 26 after fabrication of the cuff will not be subject to any external stress, leading to the rolled configuration shown in FIG. 6.

The silicone is preferably selected as the base material for the implantable cuff, due to its excellent biocompatibility properties, both in terms of bio-tolerance (the implant does not cause damage to the host with the absence of toxicity and of mechanical tissue damage) and biostability (the implant withstands conditions induced by the host).

The sheet 26 carries in the region intended to come into contact with the vagus nerve after winding (the area to the left in FIG. 4) a number of electrodes 28 reported on the surface of the sheet or embedded in the thickness of elastomeric material. These electrodes 28 are connected to wires 30 intended to be connected to the pulse generator 10. In the example illustrated in FIG. 4, these electrodes 28 are uniformly distributed along the winding axis of the cuff 26 and are interconnected so as to form a matrix of quasi-three-pole contacts (anode/cathode/anode or vice versa) connected to the corresponding microcables 30.

The cuff is made from the sheet 26 which has a rectangular shape with a width 32 forming a first side (which will come within the spiral after winding of the cuff), a second opposite side 34 forming a second width (which comes out of the cuff after winding), and two sides 36, 38 forming a first and a second lengths interconnecting the sides of the widths 32, 34.

The right angled corners of the rectangular sheet 26 are cut (by stamping, cutting blade or any other suitable manufacturing process) so as to eliminate the regions delimited by the dashed line 40, thereby forming beveled edges 42, 44, 46, 48. In the region of the side 34, the beveled edges 42 and 44 form with the lengths 36, 38 (which are parallel to the axis Δ) an angle α of 20° to 45° for example, so that the extent of the removed portion 40 to form the bevel extends over a length x of about 15 to 60% of the total length L of the sheet 26, and on a width y of the order of 20 to 50% of the total width of the sheet 26. The bevels 46, 48 on the opposite side form an angle β of 30° to 60° and extend over a width z of 10 to 25% of the total width of the sheet 26.

Furthermore, in the thickness direction, as depicted in FIG. 5, the end 32 forms a beveled edge 50, the bevel being turned toward the face of the sheet to be applied against the nerve (that is to say the face carrying the electrodes 28). This bevel is inclined by an angle γ between 20° and 45° for example.

With the configuration as described above, in its rolled configuration the cuff according to the invention takes the form shown in FIG. 6, with an appearance resembling a crescent pastry (straight shape), because of the beveled edges 42, 44, which give the outer portion of the rolled cuff a tongue-shape. This tongue facilitates implantation operations, insofar as the cuff can be handled without risk of collapse of the corners of the cuff inwardly, which would form detrimental thickness.

In addition, the shape of a "crescent" immediately makes visible a winding inadvertently reversed, that is to say, when the region carrying the electrodes (left in FIG. 4) would cover the opposite region (region on the right FIG. 4), rather than the desired configuration that is the other way around. If the winding is reversed, since bevels 46, 48 are of much smaller size than the bevels 42 and 44, the typical form with tongue as shown in FIG. 6 would be absent, immediately revealing that the winding is in reverse.

Another advantage of this crescent shape is the stiffness gradient of the cuff in the rolled configuration, the rigidity gradually decreasing from the center to the ends of the cuff. The greater flexibility allows the ends to locally exert less stress on the nerve (unlike the prior art cuffs, as shown in FIG. 2), while in the central region the clamping force exerted by the cuff is at its maximum, which helps to maintain the electrodes in support against the nerve.

To manufacture the cuff, it is possible to use relatively thin foils (on the order of 100 μm), which results in very flexible, and therefore very well tolerated sleeves without compromising ease of implantation and a very gradual transition between the nerve and the cuff.

Regarding the bevel 50, the advantage gained by this is illustrated in FIG. 7, compared with FIG. 3, which is a similar representation for a conventional cuff. In the case of the embodiment of the invention shown in FIG. 7, the material thickness is smaller in the edge 32 into contact with the region of the nerve, so that it is subjected to much less stress, thus eliminating the risk of deformation or crushing, locally sustained by the nerve.

What is claimed is:
1. An implantable lead comprising a cuff adapted to be wound around an elongate cylindrical body such as a nerve, the cuff comprising:
 a sheet of elastically deformable material having at least one detection/stimulation electrode on a first face of the sheet;
 the sheet being pre-stressed such that it is self-winding from an initial position wherein the sheet is held under stress in a deployed state to a final position wherein the sheet is loosely spirally wound to form a sleeve around the cylindrical body, with the first face carrying the at least one electrode facing inwards;
 the sheet being delimited by a first end width, a second opposite end width, a first length joining first counterpart ends of the first and the second width, and a second opposite length joining the second homologous ends of the first and the second widths,
 wherein the first end width is connected to the first and second lengths by a first and a second respective bevel edge forming an oblique angle with respect to a direction of greatest dimension of the sheet.

2. The lead of claim 1, wherein each beveled edge forms, relative to the direction of greatest dimension of the sheet, an angle between 20 and 45°.

3. The lead of claim 1, wherein each beveled edge extends across 15 to 60% of the extent of the sheet in the direction of greatest dimension.

4. The lead of claim 1, wherein each beveled edge extends across 20 to 50% of the extent of the sheet perpendicular to the direction of greatest dimension.

5. The lead of claim 1, wherein the second end width is connected to the first and second lengths by a third and a fourth respective bevel edge forming a second oblique angle relative to the direction of greatest dimension of the sheet.

6. The lead of claim 5, wherein the third and fourth beveled edges each form, relative to the direction of greatest dimension of the sheet, an angle between 30 and 60°.

7. The lead of claim 5, wherein the third and fourth beveled edges each extend across 10 to 25% of the extent of the sheet perpendicular to the direction of greatest dimension.

8. The lead of claim 1, wherein an edge of the sheet in the first width region is a chamfered edge in a thickness direction of the sheet, the chamfer being oriented toward the first face facing inwardly.

9. The lead of claim 8, wherein the chamfer forms with respect to the direction of greatest dimension of the sheet an angle between 20 and 45°.

10. The lead of claim 1, wherein the first end width defines an outer edge of the cuff after winding and the second end width defines an inner edge of the cuff after winding.

11. An electrode cuff for nerve stimulation, comprising:
a sheet of elastomer having a spiral bias so as to allow self-winding of the sheet into the cuff when unstressed; and
an electrode on a first face of the sheet;
wherein the sheet comprises the first face, a second face opposite the first face, a first side, a second side, a third side opposite the first side, and a fourth side opposite the second side;
wherein a transition between the first side and the second side includes a first beveled edge, a transition between the second side and the third side includes a second beveled edge, a transition between the third side and the fourth side includes a third beveled edge, and a transition between the fourth side and the first side, includes a fourth beveled edge; and
wherein the second side is chamfered between the first face and the second face, in a direction of the first face.

12. The electrode cuff of claim 11, wherein the first beveled edge and the second beveled edge are shorter than the third beveled edge and the fourth beveled edge.

13. The electrode cuff of claim 12, wherein the first beveled edge and the second beveled edge have the same length, and wherein the third beveled edge and the fourth beveled edge have the same length.

14. The electrode cuff of claim 11, wherein the first beveled edge and the second beveled edge each extend for 10 to 25% of a distance of the sheet between the first side and the third side.

15. The electrode cuff of claim 11, wherein the third beveled edge and the fourth beveled edge each extend for 15 to 60% of a distance of the sheet between the second side and the fourth side.

16. The electrode cuff of claim 11, wherein the third beveled edge and the fourth beveled edge each extend for 20 to 50% of a distance of the sheet between the first side and the third side.

17. The electrode cuff of claim 11, wherein the first beveled edge and the second beveled edge extend along an axis that is angularly offset between 30 and 60° relative to the first side and the third side, respectively.

18. The electrode cuff of claim 11, wherein the third beveled edge and the fourth beveled edge extend along an axis that is angularly offset between 20 and 45° relative to the third side and the first side, respectively.

* * * * *